(12) United States Patent
Jetti et al.

(10) Patent No.: US 9,725,412 B2
(45) Date of Patent: Aug. 8, 2017

(54) POLYMORPHIC FORMS OF PERINDOPRIL (L)-ARGININE AND PROCESS FOR THE PREPARATION THEREOF

(71) Applicant: Mylan Laboratories Limited, Hyderabad (IN)

(72) Inventors: Ramakoteswara Rao Jetti, Hyderabad (IN); Chetan Kanaiyalal Raval, Hyderabad (IN); Aggi Ramireddy Bommareddy, Hyderabad (IN); Debashish Datta, Hyderabad (IN)

(73) Assignee: Mylan Laboratories Limited (IN)

( * ) Notice: Subject to any disclaimer, the term of this patent is extended or adjusted under 35 U.S.C. 154(b) by 16 days.

(21) Appl. No.: 14/812,053

(22) Filed: Jul. 29, 2015

(65) Prior Publication Data

US 2015/0336890 A1 Nov. 26, 2015

Related U.S. Application Data (62) Division of application No. 14/161,967, filed on Jan. 23, 2014, now abandoned, which is a division of application No. 13/001,180, filed as application No. PCT/IN2009/000357 on Jun. 22, 2009, now Pat. No. 8,686,161.

(30) Foreign Application Priority Data

Jun. 24, 2008 (IN) .......................... 1535/CHE/2008

(51) Int. Cl.
| | | |
|---|---|---|
| *C07D 209/08* | (2006.01) | |
| *C07D 209/44* | (2006.01) | |
| *C07D 209/42* | (2006.01) | |
| *C07C 277/00* | (2006.01) | |

(52) U.S. Cl.
CPC .......... *C07D 209/44* (2013.01); *C07C 277/00* (2013.01); *C07D 209/42* (2013.01)

(58) Field of Classification Search
None
See application file for complete search history.

(56) References Cited

U.S. PATENT DOCUMENTS

| | | | |
|---|---|---|---|
| 4,508,729 A | 4/1985 | Vincent et al. | |
| 4,616,030 A | 10/1986 | Vincent et al. | |
| 4,616,031 A | 10/1986 | Vincent et al. | |
| 4,914,214 A | 4/1990 | Vincent et al. | |
| 5,061,722 A | 10/1991 | Teetz et al. | |
| 5,162,362 A | 11/1992 | Geiger et al. | |
| 6,696,481 B2 * | 2/2004 | Damien et al. ...... | C07D 209/42 514/412 |
| 7,259,181 B2 * | 8/2007 | Pfeiffer ................ | A61K 31/404 514/412 |
| 7,279,583 B2 | 10/2007 | Dubuffet et al. | |
| 7,521,566 B2 * | 4/2009 | Datta .................... | C07C 227/32 548/492 |
| 7,534,896 B2 | 5/2009 | Dubuffet et al. | |
| 7,615,571 B2 | 11/2009 | Gunjal et al. | |
| 7,846,961 B2 * | 12/2010 | Coquerel ............. | C07D 209/42 514/412 |
| 7,923,569 B2 * | 4/2011 | Coquerel ............. | C07D 209/42 548/452 |
| 7,973,173 B2 | 7/2011 | Kankan et al. | |
| 8,101,646 B2 | 1/2012 | Weeratunga et al. | |
| 2003/0158121 A1 * | 8/2003 | Pfeiffer ................ | C07D 209/42 548/492 |
| 2009/0186934 A1 * | 7/2009 | Coquerel ............. | C07D 209/42 514/419 |
| 2009/0203758 A1 * | 8/2009 | Coquerel ............. | C07D 209/42 514/412 |
| 2015/0252001 A1 * | 9/2015 | Wagh ................. | C07K 5/06026 548/452 |

FOREIGN PATENT DOCUMENTS

| | | |
|---|---|---|
| EP | 1354873 A1 | 10/2003 |
| FR | 2897865 A1 | 8/2007 |
| WO | 2007/099216 A2 | 9/2007 |
| WO | 2007/099217 A1 | 9/2007 |

OTHER PUBLICATIONS

International Search Report, PCT/IN2009/000357, dated Oct. 27, 2009.

* cited by examiner

*Primary Examiner* — Nyeemah A Grazier (57) ABSTRACT

The present invention relates to novel and stable polymorphic forms of Perindopril (L)-Arginine designated as Form γ and amorphous form and processes for their preparation. The present invention also provides the novel polymorph Form γ with greater stability to heat and humidity and can be prepared on large scale by an efficient, economic and reproducible process.

12 Claims, 6 Drawing Sheets

POLYMORPHIC FORMS OF PERINDOPRIL (L)-ARGININE AND PROCESS FOR THE PREPARATION THEREOF

CROSS REFERENCE TO RELATED APPLICATIONS

The present application is a divisional of U.S. patent application Ser. No. 14/161,967, filed on Jan. 23, 2014, which is a divisional of U.S. patent application Ser. No. 13/001,180, filed on Aug. 23, 2011, now U.S. Pat. No. 8,686,161, which application is a national phase entry under 35 U.S.C. §371 of International Application No. PCT/IN2009/000357, filed Jun. 22, 2009, published in English, which claims the benefit of Indian patent application No. 1535/CHE/2008 filed on Jun. 24, 2008, the disclosures of said applications are incorporated by reference herein.

FIELD OF THE INVENTION

The present invention provides novel polymorphic form gamma (γ) of Perindopril (L)-Arginine and amorphous form of Perindopril (L)-Arginine. The present invention also provides novel processes for the preparation of polymorphic form gamma (γ) of Perindopril (L)-Arginine and the amorphous form of Perindopril (L)-Arginine.

BACKGROUND OF THE INVENTION

Angiotensin-converting enzyme (ACE) inhibitors are used to treat high blood pressure and some types of heart failure. Perindopril, (2S)-2-[(1S)-1-carbethoxybutylamino]-1-oxopropyl-(2S,3aS,7aS)-perhydroindole-2-carboxylic acid of formula (I), is a potential (ACE) inhibitor. Perindopril erbumine salt is marketed under the brandname ACEON®.

U.S. Pat. No. 4,508,729 and EP 004965881 patents have disclosed Perindopril and its pharmaceutically acceptable salts, wherein pharmaceutically acceptable salt is selected from the group comprising mineral organic, base or acid such as the sodium salt or maleate salt. This patent also disclosed the stability of maleate and sodium salts of Perindopril. In the course of stability studies towards temperature and humidity, it is found that sodium salt is not suitable for making the formulation because it is immediately converted into oil on contact with the atmosphere. With respect to the maleate salt, it degrades rapidly under such conditions (approximately 25 to 30% of product degraded in 8 days at 50° C.).

U.S. Pat. No. 4,914,214 discloses a process for the preparation of Perindopril and its tert-butylamine salt (Perindopril erbumine). The tert-butylamine salt has exhibited the best stability compared to the other salts studied till then. But, in view of the intrinsic fragility of Perindopril, the tert-butylamine salt has not been capable of providing a complete solution to the problems of the product's stability towards heat and humidity. Indeed, for marketing tablets of Perindopril tert-butylamine salt in certain countries, additional packaging is found to be essential. Moreover, even for temperate-climate countries, the instability of the product has made it impossible to obtain a shelf-life of more than 2 years for the tablets. Finally, for marketing the tablets, they have to be marked "to be stored at a temperature less than or equal to 30 degrees".

According to the prior art, Perindopril, tert-butylamine salt is stored in a special package and requires appropriate storage conditions, thus making it a costly issue. Thus, there is a need to develop a new salt, which is having good stability in different temperatures and humidity conditions.

Numerous salts were studied and, as indicated hereinbefore, the salts customarily used in the pharmaceutical sector proved to be unstable. On the other hand, and in surprising manner, it has been found that the Arginine salt of Perindopril, besides being new, has many unexpected advantages over all the other salts studied so far, especially, over the tert-butylamine salt of Perindopril.

Perindopril Arginine represented by the formula (II), its hydrates, pharmaceutical composition and a method of treatment is first disclosed in U.S. Pat. No. 6,696,481. This patent also disclosed that the Arginine salt of Perindopril is an alternate to tert-butylamine salt having superior properties in terms of stability towards heat and humidity.

US '481 patent does not disclose the experimental details for preparation of the hydrates of Arginine salt of Perindopril. The said hydrates are not characterized by moisture content, DSC and PXRD pattern. In addition to this, the said patent claims Arginine salt of Perindopril and hydrates thereof.

WO 2007099216 claims beta (β) crystalline polymorphic form of (L)-Arginine salt of Perindopril and process for the preparation thereof.

WO 2007099217 claims alpha (α) crystalline form of the (L)-Arginine salt of Perindopril and process for the preparation thereof.

WO '216 and WO '217 patent applications provided 2θ, d-spacing values and intensity table for Form α and Form β but no PXRD pattern is disclosed. These applications further provides insufficient experimental details in each case by disclosing only a single example (example-1) for preparation of Form α and Form β.

Figure 3:
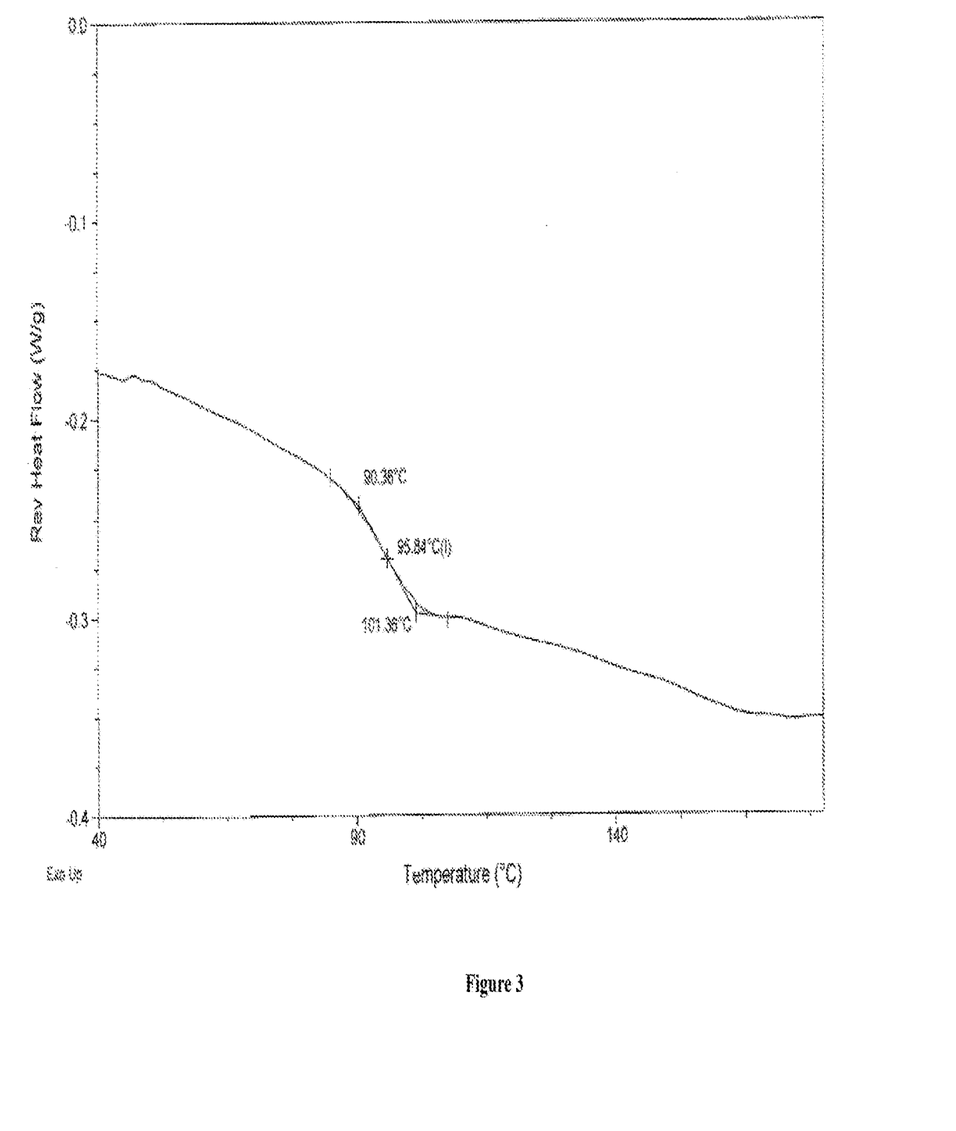
FIG. 3 is modulated DSC thermogram of amorphous Perindopril (L)-Arginine.
Figure 4:
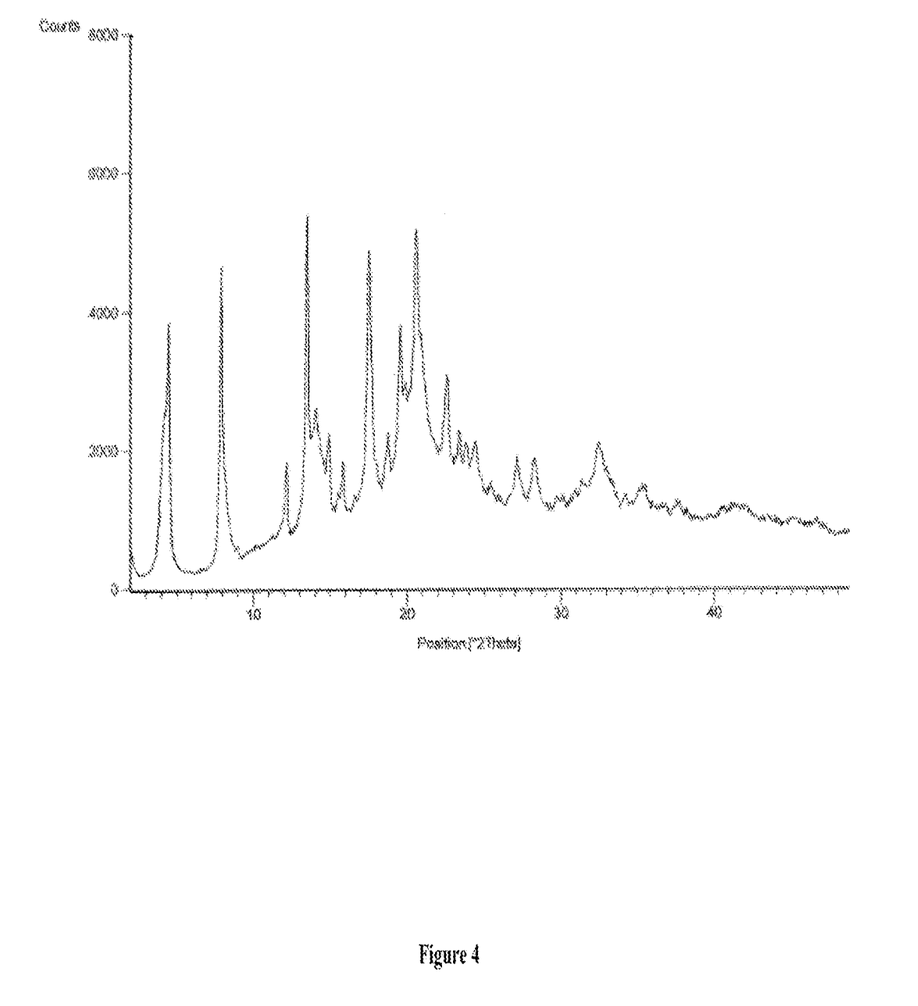
FIG. 4 is powder X-ray diffraction diagram of Perindopril (L)-Arginine Form α (as per example 1 of WO'217).
Figure 5:
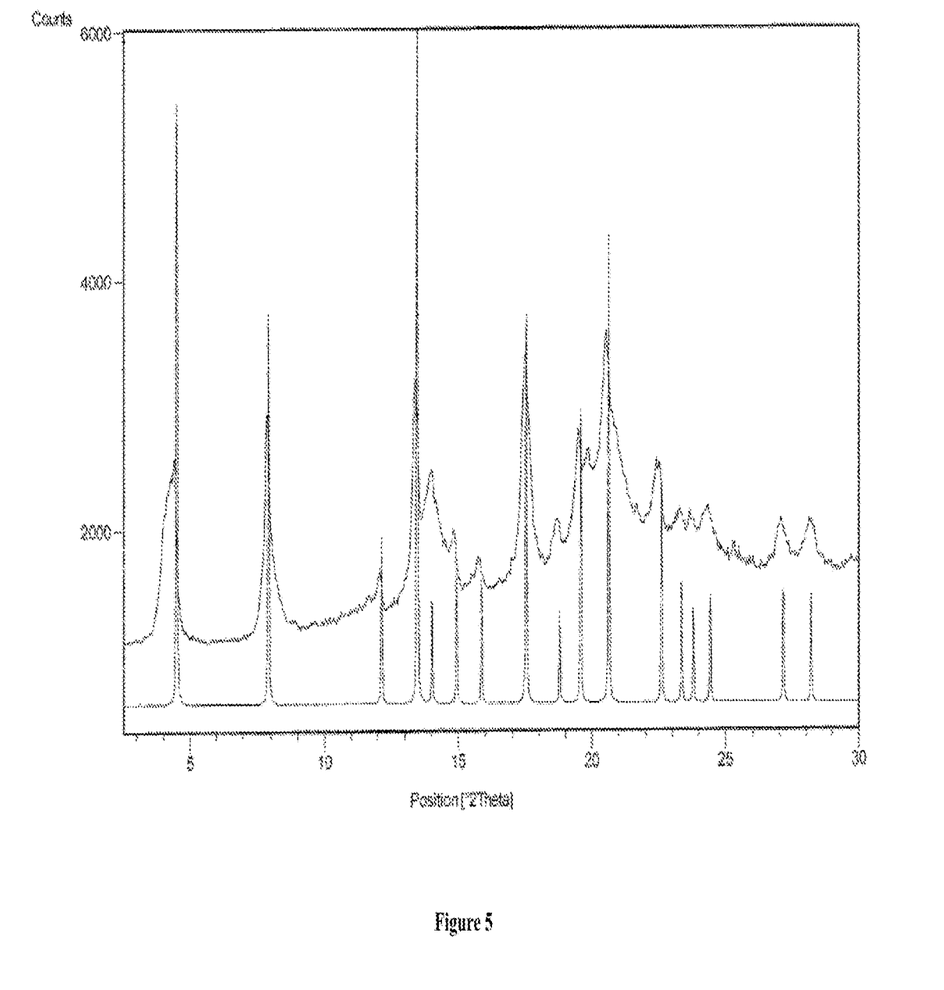
FIG. 5 is the overlay of experimental and simulated Powder X-ray diffraction diagram of Perindopril (L)-Arginine Form α.

According to WO '217 English translation, in Example 1, crystalline Form α is prepared by dissolving 1:1 molar ratio of Perindopril and (L)-Arginine in water at ambient temperature under stirring, followed by addition of methylcyclohexane and then dimethylsulfoxide. The solution is cooled to 20° C. and maintained under stirring. The solid obtained is filtered, washed and dried. The reproduction of Example 1 of WO'217 in our laboratories afforded Form α inconsistently (success rate 10%) with characteristic peaks as disclosed in WO '217 application (FIG. 3). We further simulated the PXRD pattern of Form α from the literature data (WO '217 PXRD table) which is similar to our experimental PXRD pattern (FIG. 4). The water content of the experimental Form α is in the range of 3-4% which further confirms that the form α is a hydrate, preferably monohydrate.

According to WO '216 English translation, Example 1, crystalline Form β is prepared by dissolving the salt of (L)-Arginine of Perindopril in acetonitrile at reflux temperature. After 1 hour stirring under reflux, the crystals obtained are filtered at a temperature of 80° C. The crystals obtained are dried, which leads to Form β in anhydrous form. However, the reproduction of Example 1 of WO'216 in our laboratories never obtained Form β. Also we attempted several other process variations for the preparation of Form β such as starting from 1:1 molar ratios of Perindopril and (L)-Arginine or from Perindopril (L)-Arginine salt using different solvent combinations at different temperatures but we failed to reproduce Form β.

According to WO '216 crystalline form β is an anhydrous form which prompted us to look at several other processes techniques to remove moisture from Form α (monohydrate) such as azeotropic distillation and/or by drying. But even after reducing the moisture content below 1% (Table-2) we failed to obtain Form β. From this it appears that WO'216 application process is not suitable for the preparation of form β or polymorphic form β in an elusive form.

In view of the above prior problems, there is an unmet need for a stable form of Perindopril (L)-Arginine which can be prepared by an efficient, economic and reproducible process, particularly to large scale preparation. Further it should be suitable for handling and have excellent physical and chemical stability towards heat and humidity at different conditions.

Amorphous forms of an API are characterized by decreasing amounts of long range order in the solid state and may enjoy enhanced properties with respect to crystalline forms of the solid. Also relevant is the degree of amorphous character. Crystallinity and amorphicity are continuous properties and a particular solid may have a degree of crystallinity that ranges from 0% (fully amorphous) to 100% (fully crystalline). The structural basis for losses in crystallinity could arise from progressive "decrystallization" throughout the solid or through a growth of amorphous regions within the crystalline matrix (Polymorphism: in the Pharmaceutical Industry, R. Hilfiker (Ed.), Wiley-VCH, Weinheim, Chapter 10, pp. 259-285, 2006). It is noted that no amorphous forms of Perindopril (L)-Arginine are satisfactorily characterized.

OBJECTIVE OF THE INVENTION

The main object of the present invention is to provide novel polymorphic form gamma (γ) of Perindopril (L)-Arginine.

Another object of the present invention is to provide Perindopril (L)-Arginine (γ) form having the degree of crystallinity under 60%.

Yet another object of the present invention is to provide novel process for the preparation of novel polymorphic form gamma (γ) of Perindopril (L)-Arginine.

Yet another object of the present invention is to provide a thermodynamically more stable polymorphic form γ of Perindopril (L)-Arginine which has enhanced physical and chemical stability towards heat and humidity, than prior art.

The main object of the present invention is to provide novel amorphous form of Perindopril (L)-Arginine.

Another object of the present invention is to provide novel process for the preparation of amorphous Perindopril (L)-Arginine.

SUMMARY OF THE INVENTION

In one aspect of the present invention relates to novel and stable polymorphic form of Perindopril (L)-Arginine salt designated as Form gamma (γ).

Figure 1:
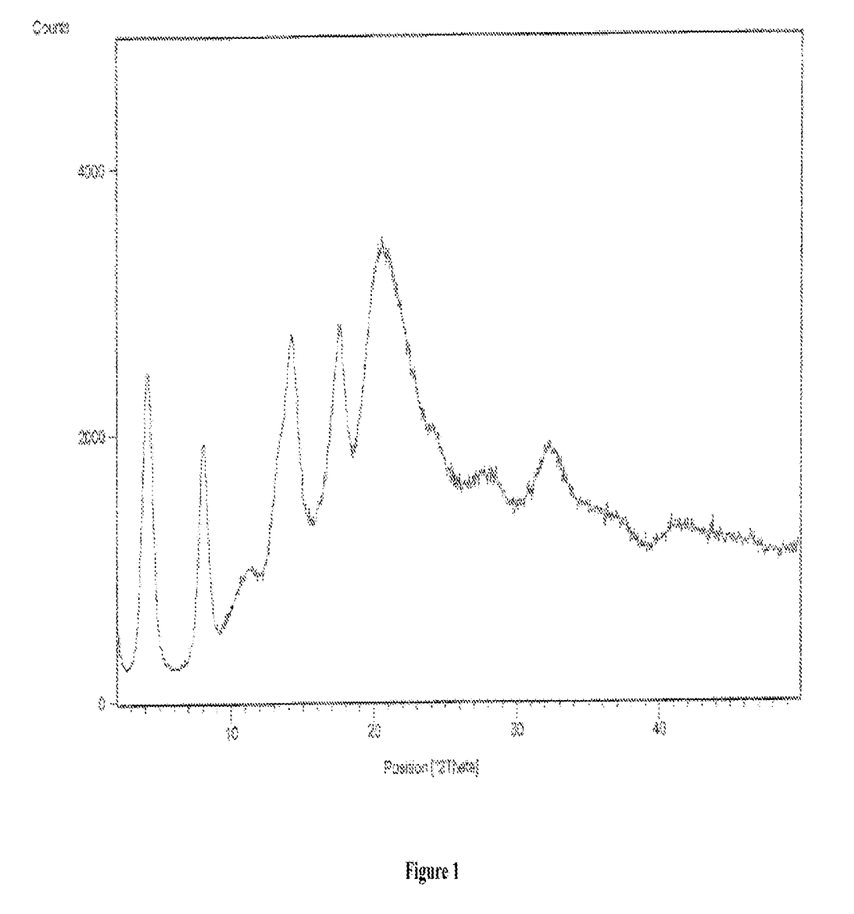
FIG. 1 is powder X-ray diffraction diagram of Form γ of Perindopril (L)-Arginine.

In another aspect, the present invention relates to novel polymorphic form γ of Perindopril (L)-Arginine, characterized by a powder X-ray diffraction pattern and shown in FIG. 1.

In yet another aspect, the present invention relates to novel polymorphic form γ of Perindopril (L)-Arginine, characterized by a powder X-ray diffraction pattern with peaks at about 4.21, 7.87, 13.19, 14.12, 17.60, 20.15±0.2 degrees 2-Theta.

In yet another aspect of the present invention is to provide Perindopril (L)-Arginine (γ) form having the degree of crystallinity under 60%.

In yet another object of the present invention is to provide a thermodynamically more stable polymorphic form gamma (γ) of Perindopril (L)-Arginine which has enhanced physical and chemical stability towards heat and humidity, when compared to the prior art.

In yet another object of the present invention is to provide a novel process for the preparation of novel polymorphic form gamma (γ) of Perindopril (L)-Arginine.

In another aspect, the present invention relates to a novel process for the preparation of the polymorphic Form γ of Perindopril (L)-Arginine comprising the steps of a) dissolving Perindopril in water or suitable organic solvent b) adding (L)-Arginine c) removing the solvent and d) isolating novel polymorphic form γ of Perindopril (L)-Arginine.

In yet another aspect, the present invention relates to a novel process for the preparation of polymorphic form γ of Perindopril (L)-Arginine comprising the steps of a) dissolving Perindopril (L)-Arginine in suitable organic solvent b) adding suitable antisolvent and c) isolating novel polymorphic form γ of Perindopril (L)-Arginine.

In yet another aspect, the present invention relates to a novel process for the preparation of polymorphic form γ of Perindopril (L)-Arginine comprising the steps of a) suspending Perindopril free acid and Arginine in suitable organic solvent at room temperature b) heating the reaction mixture to reflux temperature followed by azeotropic distillation c) adding suitable antisolvent and d) isolating novel polymorphic form γ of Perindopril (L)-Arginine.

In yet another aspect, the present invention relates to a novel process for the preparation of polymorphic form γ of Perindopril (L)-Arginine comprising the steps of a) suspending Perindopril free acid and Arginine in suitable organic solvent b) heating the reaction mass to reflux temperature to get clear solution c) cooling the reaction mass d) adding suitable antisolvent and e) isolating novel polymorphic form γ of Perindopril (L)-Arginine.

In yet another aspect, the present invention relates to a novel process for the preparation of polymorphic form γ of Perindopril (L)-Arginine comprising the steps of a) dissolving perindopril free acid and arginine in water at ambient temperature b) adding the first solvent c) cooling the resulting solution of step b) then addition of second solvent and d) isolating novel polymorphic form γ of Perindopril (L)-Arginine.

In yet another aspect, the present invention relates to a novel process for the preparation of polymorphic form γ of Perindopril (L)-Arginine comprising the steps of a) dissolving perindopril free acid in suitable organic solvent or mixture of organic solvent b) adding arginine solution by dissolving arginine in water and c) isolating novel polymorphic form γ of Perindopril (L)-Arginine.

In yet another aspect, the present invention relates to a novel process for the preparation of polymorphic form γ of Perindopril (L)-Arginine comprising the steps of a) suspending perindopril arginine in appropriate solvents b) stirring the resulting slurry of step a) at different temperature and c) isolating novel polymorphic form γ of Perindopril (L)-Arginine.

In yet another aspect, the present invention relates to a novel process for the preparation of polymorphic form γ of Perindopril (L)-Arginine by exposing amorphous or α form of Perindopril (L)-Arginine salt to a relative humidity (RH) more than 90% for several hours (table-2), indicating that α form and amorphous form of Perindopril (L)-Arginine are metastable.

In yet another aspect, the present invention relates to hygroscopic stability of the novel polymorphic form γ of Perindopril (L)-Arginine. The hygroscopic studies shows that there is no substantial increase in moisture content for Form γ when stored in different relative humidities for a period of 1 to 3 months suggesting that Form γ is stable to humidity.

In yet another aspect, the present invention relates to the conversion of metastable polymorphs of Perindopril (L)-Arginine such as the fully amorphous form and the α form into the stable polymorphic form γ of Perindopril (L)-Arginine. The process comprises the steps of suspending the fully amorphous form or the α form of Perindopril (L)-Arginine salt in a solvent or mixture of solvents and stirring at room temperature for several hours, and then isolating the polymorphic form γ of Perindopril (L)-Arginine.

In yet another aspect, the present invention relates to stability, solubility and storage profile of the novel polymorphic form γ of Perindopril (L)-Arginine.

In yet another aspect the present invention relates to amorphous form of Perindopril (L)-Arginine salt.

Figure 2:
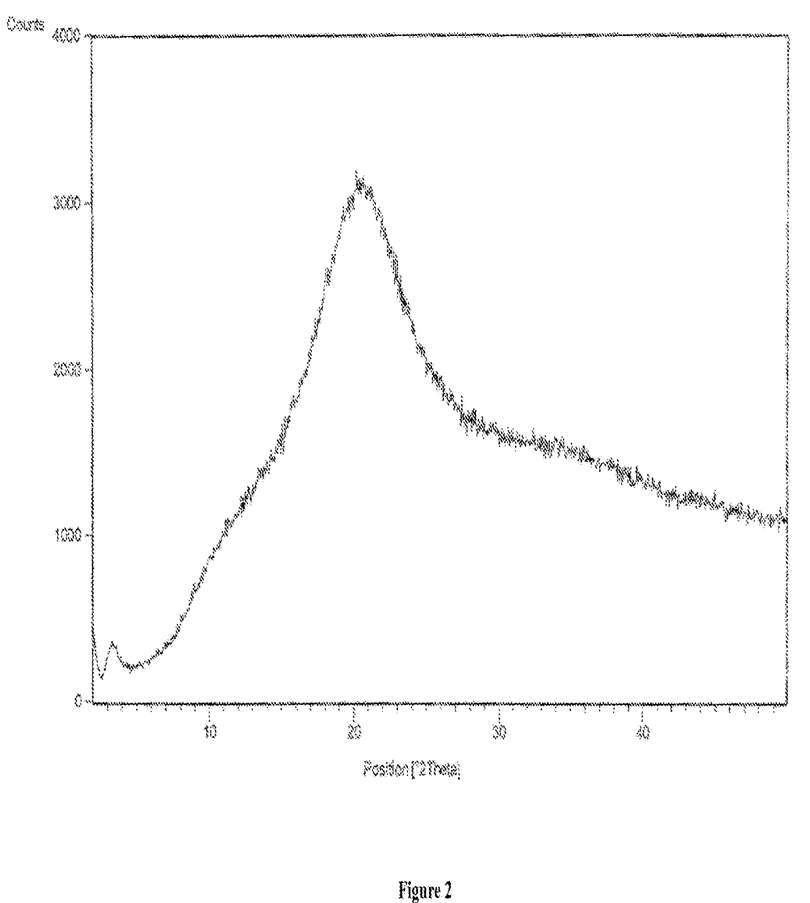
FIG. 2 is powder X-ray diffraction diagram of amorphous Perindopril (L)-Arginine.

In yet another aspect, the present invention relates to amorphous form of Perindopril (L)-Arginine characterized by a powder X-ray diffraction pattern, shown in FIG. 2.

In yet another aspect, amorphous form of Perindopril (L)-Arginine salt is further characterized by a glass transition temperature (Tg) at 95.84° C. in DSC, shown in FIG. 3.

In yet another aspect, the present invention relates to novel process for the preparation of amorphous form of Perindopril (L)-Arginine salt comprising the steps of a) dissolving Perindopril (L)-Arginine salt in a suitable organic solvent b) removing the solvent and c) isolating amorphous form of Perindopril (L)-Arginine salt.

In yet another aspect, the present invention relates to novel process for the preparation of amorphous form of Perindopril (L)-Arginine salt comprising the steps of a) suspending Perindopril in a solvent or mixture of solvents b) heating the reaction mass temperature to reflux followed by cooling room temperature c) removing the solvent and d) isolating amorphous form of Perindopril (L)-Arginine.

Powder X-ray Diffraction (PXRD)

The PXRD measurements were carried out using PANalytical, X'Pert PRO powder diffractometer equipped with goniometer of θ/θ configuration and X'Celerator detector. The Cu-anode X-ray tube is operated at 40 kV and 30 mA. The experiments were conducted over the 2θ range of 2.0°-50.0°, 0.030° step size and 50 seconds step time.

Karl-Fisher

Water content was determined on Metrohm Karl-Fisher titrator (Model: 794 Basic Titrino) using pyridine free single solution (Merck, Mumbai) with sample mass between 450 mg to 550 mg.

DSC Glass Transition

The glass transition temperature (Tg) of the amorphous Perindopril (L)-Arginine was measured on TA Q1000 of TA instruments with modulated DSC software. The sample were heated from 40 to 180° C. at heating rate of 5.0° C./min with modulation amplitude ±0.5° C., the modulation period 80 sec and nitrogen purging at a flow rate of 50 ml/min. Standard aluminum pans covered by lids with five pin holes were used.

Polarising Light Microscopy (PLM)

Polarising Light Microscopy (DFC-280, Mikroscope Leica DMEP, Germany) was used to determine whether the samples contained birefringence. They were examined using a 40-fold magnification.

Scanning Electron Microscopy (SEM)

The samples were mounted onto a strip of double-sided carbon tape and sputter coated with a thin layer of platinum under vacuum prior to analysis. SEM was performed on JEOL, JSM 6380 instrument using a 2 kV beam acceleration voltage.

DETAILED DESCRIPTION OF THE INVENTION

The present invention relates to a novel polymorphic form of Perindopril (L)-Arginine salt designated as Form gamma (γ). The present invention also relates to a novel fully amorphous form of Perindopril (L)-Arginine salt. The invention further relates to novel processes for the preparation of novel polymorphic form γ and the fully amorphous form of Perindopril (L)-Arginine salt. The present invention also provides Perindopril (L)-Arginine (γ) form having a degree of crystallinity under 60% with enhanced stability with respect to heat and humidity.

The said forms are differ from each other in their physical properties, and spectral data and method of preparation and are characterized by their Powder X-ray Diffraction patterns, differential scanning calorimetry (DSC), polarizing microscopy (PLM), scanning electron microscopy (SEM) and/or by Karl-Fisher (KF) method.

In one embodiment, the present invention provides a novel polymorphic form γ of Perindopril (L)-Arginine, characterized by a powder X-ray diffraction pattern with peaks at about 4.21, 7.87, 13.19, 14.12, 17.60, 20.15±0.2 degrees 2-theta, shown in FIG. 1.

The present invention is to provide Perindopril (L)-Arginine (γ) form having the degree of crystallinity under 60%, which has enhanced stability to heat and humidity. According to the present invention, the obtained Perindopril (L)-Arginine (γ) form is subjected to accelerated stability at 40° C. and relative humidity (RH) 75%. The polymorphic form γ of Perindopril (L)-Arginine is found to be chemically and physically very stable. There is no substantial increase in the moisture content that is observed. The PXRD pattern remains the same as initially and no degradation is observed in HPLC.

According to the present invention, there is provided a novel process for the preparation of novel polymorphic form γ of Perindopril (L)-Arginine comprising the steps of a) dissolving perindopril free acid in water b) adding (L)-Arginine c) removing the solvent and d) isolating novel polymorphic form γ of Perindopril (L)-Arginine.

In one of the embodiments of the present invention, Perindopril free acid is dissolved in water to get clear solution at room temperature. (L)-Arginine is added to the solution and it is maintained for 15 to 30 minutes at room temperature. The solvent is removed by using techniques such as vacuum distillation, freeze drying and spray drying to obtain the polymorphic form γ of Perindopril (L)-Arginine.

According to the present invention, there is provided a novel process for the preparation of the novel polymorphic form γ of Perindopril (L)-Arginine comprising the steps of a) dissolving Perindopril (L)-Arginine in suitable organic solvent at room temperature b) adding suitable antisolvent and c) isolating novel polymorphic form γ of Perindopril (L)-Arginine.

In one of the embodiments of the present invention, Perindopril (L)-Arginine is dissolved in a solvent selected from alcohol such as methanol, ether solvent such as 1,4-dioxane, polar solvents such as pyridine, N-methyl pyrrolidone at room temperature. Antisolvent is added to the above clear solution at room temperature followed by stirring to obtain the polymorphic form γ of Perindopril (L)-Arginine. Anti-solvent used for the precipitation is selected from ester solvent such as ethyl acetate, ketone solvent such as acetone, ether solvent such as isopropyl ether or mixtures thereof;

According to the present invention, there is provided a novel process for the preparation of novel polymorphic form γ of Perindopril (L)-Arginine comprising the steps of a) suspending Perindopril and (L)-Arginine in suitable organic solvent at room temperature b) heating the reaction mass to reflux temperature followed by azeotropic distillation c) adding suitable antisolvent d) isolating novel polymorphic form γ of Perindopril (L)-Arginine.

In one of the embodiments of the present invention, Perindopril (L)-Arginine is suspended in a suitable organic solvent selected from aromatic hydrocarbons such as toluene, tetrahydrofuran, dichloroform, dichloroethane or mixtures thereof. The resulting slurry is heated to reflux temperature (70 to 115° C.) to remove the water by azeotropic distillation. The antisolvent is added at reflux temperature, followed by cooling of the resulting solution to room temperature. The antisolvent used is selected from ethyl acetate or acetonitrile or mixtures thereof.

According to the present invention, there is provided a novel process for the preparation of novel polymorphic form γ of Perindopril (L)-Arginine comprising the steps of a) suspending Perindopril free acid and Arginine in suitable organic solvent b) heating the reaction mass to reflux temperature to get clear solution c) cooling the reaction mass d) adding suitable antisolvent and e) isolating novel polymorphic form γ of Perindopril (L)-Arginine.

In one of the embodiments of the present invention, Perindopril free acid and Arginine is suspended in a suitable organic solvent selected from alcohol such as methanol. The resulting slurry is heated to reflux temperature (50 to 70° C.) to give clear solution, which is cooled to 0 to 10° C. Antisolvent used for the precipitation is selected from ether such as t-butyl methyl ether, diisopropyl ether, diethyl ether or mixtures thereof.

According to the present invention, there is provided a novel process for the preparation of novel polymorphic form γ of Perindopril (L)-Arginine comprising the steps of a) dissolving Perindopril free acid and (L)-Arginine in water at ambient temperature b) adding the first solvent c) cooling the resulting solution of step b) then addition of second solvent and d) isolating novel polymorphic form γ of Perindopril (L)-Arginine.

In one of the embodiments of the present invention, Perindopril free acid and (L)-Arginine is dissolved in water at temperature 20 to 35° C. to get clear solution. First solvent is added at same temperature and is selected from aliphatic hydrocarbon such as cyclohexane, hexane, aromatic hydrocarbon such a toluene or mixtures thereof. The resulting mixture is cooled to 10 to 20° C.; second solvent is added at 10 to 20° C. The second solvent is selected from a polar solvent such as N-methyl pyrrolidone, polar aprotic solvent is N, N-dimethyl formamide, N,N-dimethylacetamide or mixtures thereof.

According to the present invention, there is provided a novel process for the preparation of novel polymorphic form γ of Perindopril (L)-Arginine comprising the steps of a) dissolving Perindopril free acid in suitable organic solvent b) adding (L)-Arginine solution by dissolving (L)-Arginine in water and c) isolating novel polymorphic form γ of Perindopril (L)-Arginine.

In one of the embodiments of the present invention, Perindopril acid is dissolved in suitable solvent is selected from mixture of water and organic solvent. The organic solvent is selected from alcohol such as ethanol, ketone such as acetone, ether such as 1,4-dioxane. (L)-Arginine is dissolved in water to get solution is added to the above solution followed by stirring and filtration to give polymorphic form γ of Perindopril (L)-Arginine.

According to the present invention, there is provided a novel process for the preparation of novel polymorphic form γ of Perindopril (L)-Arginine comprising the steps of a) suspending perindopril arginine in suitable solvents b) stirring the resulting slurry of step a) at different temperature and c) isolating novel polymorphic form γ of Perindopril (L)-Arginine.

In one of the embodiment of the present invention, Perindopril (L)-Arginine is selected from Perindopril (L)-Arginine polymorphic form alpha (α), Perindopril (L)-Arginine polymorphic form γ or Perindopril (L)-Arginine amorphous form. Perindopril Arginine is suspended in a solvent selected from aliphatic hydrocarbons such as n-heptane, aromatic hydrocarbon such as toluene, nitrile such as acetonitrile or mixtures thereof. The resulting slurry is stirred at temperature 20 to 115° C. followed by filtration to give polymorphic form γ of Perindopril (L)-Arginine.

According to the present invention, there is provided a novel process for the preparation of polymorphic form γ of Perindopril (L)-Arginine form by exposing form α or amorphous form of Perindopril (L)-Arginine to a relative humidity (RH>90%) for several hours indicating that α form and amorphous form of Perindopril (L)-Arginine are metastable.

According to the present invention, there is provided a hygroscopic stability of the novel polymorphic form γ of Perindopril (L)-Arginine. The hygroscopic studies shows that there is no substantial increase in moisture content for Form γ when stored in different relative humidities for a period of 1 to 3 months suggesting that Form γ is stable to humidity.

In yet another embodiment, the present invention relates to stability, solubility and storage profile of the novel polymorphic form γ of Perindopril (L) Arginine as defined herein briefly.

According to the present invention, there is provided an amorphous form of Perindopril (L)-Arginine salt.

According to the present invention, there is provided an amorphous form of Perindopril (L)-Arginine having a PXRD pattern as shown in FIG. 2. The amorphous form of Perindopril (L)-Arginine salt is further characterized by a glass transition temperature (Tg) at 95.84° C. in MDSC, shown in FIG. 3.

According to the present invention, there is provided a novel process for the preparation of amorphous form of Perindopril (L)-Arginine salt comprising the steps of a) dissolving polymorphic γ form of Perindopril (L)-Arginine in a suitable organic solvent b) removing the solvent by distillation c) isolating amorphous form of Perindopril (L)-Arginine.

In one embodiment of the present invention, Perindopril (L)-Arginine polymorphic form (γ) is dissolved in solvent selected from alcohol such as methanol to get the clear solution. The solvent is removed by distillation with or without reducing pressure to give amorphous form of Perindopril (L)-Arginine.

According to the present invention, there is provided a novel process for the preparation of amorphous form of Perindopril (L)-Arginine salt comprising the steps of a) suspending Perindopril (L)-Arginine in a solvent or mixture of solvents b) heating the reaction mass to reflux temperature followed by cooling to room temperature c) removing the solvent and d) isolating amorphous form of Perindopril (L)-Arginine.

In one embodiment of the present invention, Perindopril (L)-Arginine is suspended in a solvent or mixture of solvent selected from alcohols such as methanol, ethanol, chlorinated solvents such as dichloromethane, dichloroethene or mixture of solvents with water. The resulting slurry is heated to reflux temperature to get clear solution, which is cooled to room temperature. Solvent is removed by distillation or spray drying to give the fully amorphous form of Perindopril (L)-Arginine.

Solid State Stability

The solid state stability of the novel polymorphic form γ of Perindopril (L)-Arginine was determined by storing approximately 3.0 g of the sample at accelerated stress conditions (40° C./75% relative humidity) for 15 days, 1 month and 2 months. The samples were tested by PXRD, Karl-Fisher titrator and HPLC for final purity and degradation products. The results are given in the following Table 1.

TABLE 1

| Conditions | PXRD | m/c (%) | Purity (%) |
|---|---|---|---|
| Initial | Form γ | 3.8 | 99.1 |
| After 15 days | Same as initial | 4.2 | 99.2 |

TABLE 1-continued

| Conditions | PXRD | m/c (%) | Purity (%) |
|---|---|---|---|
| After 1 month | Same as initial | 4.4 | 99.2 |
| After 2 months | Same as initial | 5.0 | 99.1 |

The polymorphic form γ of Perindopril (L)-Arginine was found to be chemically and physically very stable. There is no substantial increase in moisture content was observed. The PXRD pattern remains same as initial and there is no degradation observed in HPLC.

Physical Stability

The physical stability of the amorphous form, Form γ and literature Form α of Perindopril (L)-Arginine was determined by storing approximately 3.0 g of the sample a) at 50° C., b) at 70° C., c) at 100° C. and d) at 90% Relative Humidity (RH). The samples are tested by PXRD and Karl-Fisher titrator after 15 hours and 72 hours. There is no change in form observed in Form γ under both drying and humid conditions but literature Form α and amorphous form are converted to Form γ in humidity. The results are shown in the following Table 2.

TABLE 2

| Conditions | Input | Period | Results |
|---|---|---|---|
| Drying | Form α at 70° C. | 3 days | Form α |
| | Form α at 100° C. | 7 days | |
| | Form γ at 70° C. | 3 days | Form γ |
| | Form γ at 100° C. | 7 days | |
| | Amorphous at 25° C. | 3 hrs | Form γ |
| Humidity (RH >90%) | Form α | 15 hrs | Form γ |
| | Form γ | 15 hrs | |
| | Amorphous | 3 hrs | |

Transformation Kinetics

Solvent-mediated polymorph transformations are an effective method to measure the physical stability for both metastable and thermodynamically stable polymorphs [1]. This study is carried out by slurring 1 g of Form γ, amorphous and literature Form α of Perindopril (L)-Arginine salt in different solvents at 25 to 30° C. for several hours. The solid samples are then characterized by PXRD (example 10, Table 6). No discernible form conversion or dissociation was observed in heptane for polymorphs Form α and Form γ but form α and amorphous form are converted to form γ while stirred in toluene or acetonitrile for more than 15 hrs at room temperature (Example 10, Table 6).

The above mentioned observations indicate that the novel polymorphic form γ of Perindopril (L)-Arginine is thermodynamically more stable than Perindopril (L)-Arginine amorphous and form α.

Crystallinity Index

The Crystallinity index is measured quantitatively from the X-ray powder diffractogram by comparing the area of the crystalline peaks (AC) to the area under the halo-shaped amorphous peak. Thus (AC+AA) equals the total scattered intensity. The Crystallinity is representing by the formula: CI=AC*100/(AC+AA). CI is estimated considering the error of ±5%, due to fluctuation in the baseline. We measured the CI of the novel Form γ prepared using different methods. The results are shown in below Table 3.

TABLE 3

| S. No. | Method | Polymorph | Crystallinity Index (%) |
|---|---|---|---|
| 1 | Freeze drying | Form γ | 14 |
|  |  |  | 15 |
|  |  |  | 15 |
| 2 | Anti solvent |  | 13 |
|  |  |  | 15 |
|  |  |  | 26 |
|  |  |  | 45 |

From above table it was observed that the crystallinity of Form γ is in the range of 10 to 60%, preferably between 10 to 45%.

Polarizing Light Microscopy (PLM)

PLM is very effective tool and can be utilized to differentiate between amorphous and crystalline substances. Generally the effects of birefringence are observed only in crystalline systems and even small amount of crystallinity can be detected by PLM.

The three different polymorphs of Perindopril (L)-Arginine salt, literature Form α and novel Form γ and amorphous form are analyzed by PLM. Form γ showed small areas of birefringence which indicate that Form γ may exist in a substantially amorphous state with residual crystallinity. This is also supported by the crystallinity index (CI) data from PXRD analysis.

Scanning Electron Microscopy (SEM)

Figure 6:
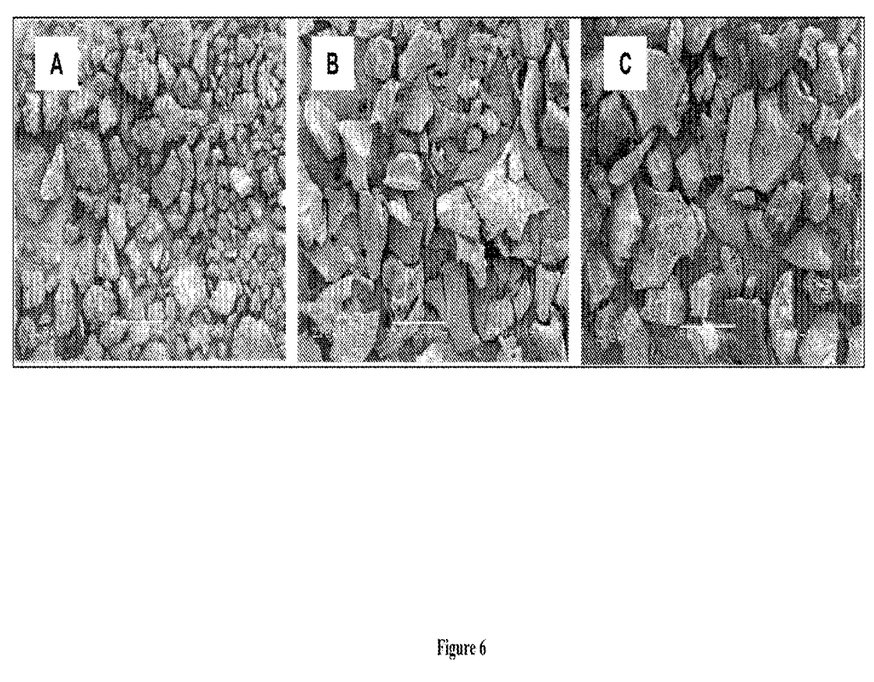
FIG. 6 is SEM images of A) Form α, B) Amorphous and C) Form γ of Perindopril (L)-Arginine salt.

SEM was used to obtain more information about the surface and the morphology of three different polymorphs of Perindopril (L)-Arginine salt (FIG. 6). Form α samples showed irregular granular type particles with rough surface. Amorphous form showed particles of different sizes with a smooth surface, more in line with the expected appearance of amorphous organic particles. Form γ has similar particle nature as amorphous however in some regions small agglomerates were observed on the smooth surface. This further hints Form γ may exist in a substantially amorphous state with traces of residual crystallinity.

Thermal Analysis

Perindopril (L)-Arginine salt Form α and Form γ have very broad melting which is in the range of 128-136° C. It was very difficult to distinguish these two forms by their melting point. Amorphous form of Perindopril (L)-Arginine salt has been studied by modulated temperature differential scanning calorimetry (MDSC) for determination of its glass transition temperature (Tg). The MTDSC experiment was carried out to separate the reversing glass transition and non-reversing relaxation endotherm. The MDSC response of amorphous form of Perindopril (L)-Arginine salt shows reversible heat flow as shown in FIG. 2 with glass transition temperature (Tg) at 95.84° C.

The following non-limiting examples illustrate specific embodiments of the present invention. They are not intended to be limiting the scope of present invention in any way.

EXPERIMENTAL SECTION

Example 1

Process for the Preparation of Amorphous Perindopril (L)-Arginine 15 g of form γ of Perindopril (L)-Arginine was dissolved in methanol (100 ml) at room temperature. The solution was filtered through hyflow bed to remove the undissolved particulates. The resulting solution was distilled out completely under vacuum at 50° C. till it was free powder. The solid obtained was identified as amorphous Perindopril Arginine.

Example 2

Preparation of Amorphous Perindopril (L)-Arginine 15 g of Perindopril was suspended in methanol (105 ml) at room temperature. To this solution (L)-Arginine (7.1 g) was added and heated to reflux to get clear solution. The resulting solution was filtered through hyflow bed to remove any undissolved particulate. The filtrate was cooled to room temperature and subjected to spray drying to give amorphous Perindopril (L)-Arginine.

Example 3

Preparation of Amorphous Perindopril (L)-Arginine 10 g of Perindopril was suspended in a 1:1 mixture of methanol and water (5:5 v/v) of dichloromethane (250 ml) at room temperature. To this solution (L)-Arginine (7.1 g) was added and heated to reflux to get clear solution. The resulting solution was filtered through hyflow bed to remove any undissolved particulate. The filtrate is then cooled to room temperature and subjected to spray drying to give amorphous Perindopril (L)-Arginine.

Example 4

Process for the Preparation of Polymorphic Form γ of Perindopril (L)-Arginine 10 g of Perindopril free acid was dissolved in water (100 ml) and added (L)-Arginine (4.7 g) and stirred for 15 minutes to get clear solution. The resulting solution was filtered through hyflow bed to remove the undissolved particulate. The resulting clear solution was subjected to freeze drying. The solid obtained is identified as form γ of Perindopril (L)-Arginine.

Example 5

Process for the Preparation of Polymorphic Form γ of Perindopril (L)-Arginine 10 g of Perindopril free acid was dissolved in water (100 ml) at room temperature. To this solution (L)-Arginine (4.7 g) was added and the resulting solution was subjected to spray drying using Buchi mini-spray dryer, (Model: B-290). The solid obtained was identified as form γ of Perindopril (L)-Arginine.

Example 6

Process for the Preparation of Polymorphic Form γ of Perindopril (L)-Arginine 5 g of Perindopril free acid and (L)-Arginine (2.3 g) were suspended in toluene (25 ml) at room temperature. The reaction mass was then reflux azeotropically for 60 minutes to get the clear solution. To this clear solution acetonitrile (250 ml) was added and stirred for 60 minutes at 75 to 80° C. The resulting solid was filtered and washed with acetonitrile (20 ml). The product obtained was identified as form γ of Perindopril (L)-Arginine.

Example 7

Process for the Preparation of Polymorphic Form γ of Perindopril (L)-Arginine 5 g of Perindopril free acid and (L)-Arginine (2.3 g) is suspended in methanol (50 ml) at room temperature. The reaction mass was then refluxed to get the clear solution and stirred for 60 minutes at 60 to 70° C. The resulting solution was cooled to room temperature and then cooled to 0 to 5° C. To this solution IPE (1.0 lit) was added and then maintained for 1 hour at 0 to 5° C. The solid obtained is dried for 15 hours under vacuum at 50° C.

Example 8

Process for the Preparation of Polymorphic Form γ of Perindopril (L)-Arginine 2 g of pure Perindopril free acid and (L)-Arginine (0.9 g) are dissolved in 10 ml of water at 25 to 30° C. To this clear solution indicated solvents at the indicated volumes was added at 25 to 30° C. and stirred for 30 minutes. The resulting solution was cooled to 15 to 20° C. and an indicated anti solvent at the indicated volumes are added slowly. The resulting reaction mass was stirred for 1 hour at 15 to 20° C. The solid was filtered and washed with 5 ml of indicated solvents. The wet solid was dried at 50 to 55° C. under vacuum for 12 hours. The results are shown in following table 4

TABLE 4

| Process | Input | Solvents | Result |
| --- | --- | --- | --- |
| Antisolvent | Perindopril + (L)-Arginine + water | CyH/DMF | Form γ |
| | | CyH/NMP | Form γ |
| | | Toluene/DMF | Form γ |
| | | Toluene/DMA | Form γ |
| | | Toluene/NMP | Form γ |

Example 9

Process for the Preparation of Polymorphic Form γ of Perindopril (L)-Arginine 5 g of Perindopril free acid was dissolved in appropriate solvents (10 ml) at room temperature and solution of (L)-Arginine (2.3 g) in water (6 ml) was added to it and stirred for 2 hours. The results obtained are represented in Table 5

TABLE 5

| Solvents | Volume ratio | Result |
| --- | --- | --- |
| Acetone/water | 2:1 | Form γ |
| Ethanol/water | 2:1 | Form γ |
| 1,4 Dioxane/water | 2:1 | Form γ |

Example 10

Process for the Preparation of Polymorphic Form γ of Perindopril (L)-Arginine 1 g of Perindopril (L)-Arginine salt is suspended in appropriate solvents at different temperature and stirred for 12 hours to afford form γ of Perindopril (L)-Arginine. The results obtained are displayed in Table 6

TABLE 6

| Input | Solvent | Volume | Temp. (° C.) | Result |
| --- | --- | --- | --- | --- |
| Form α | ACN | 5 | 25-30 | Form γ |
| | ACN | 5 | 70-80 | Form γ |
| | Toluene | 5 | 25-30 | Form γ |
| | n-heptane | 5 | 25-30 | Form α |
| Form γ | ACN | 10 | 80 | Form v |
| | Toluene | 10 | 110 | Form γ |
| | n-heptane | 10 | 60-80 | Form γ |
| Amorphous | ACN | 10 | 25-30 | Form γ |

Example 11

Process for the Preparation of Polymorphic Form γ of Perindopril (L)-Arginine 1 g of Perindopril (L)-Arginine salt is suspended in appropriate solvents at different temperature and subjected to various crystallization techniques to afford Perindopril Arginine form γ. The results obtained are displayed in Table 7

TABLE 7

| Input | Process | Solvents | Volume ratio | Temp (° C.) | Result |
| --- | --- | --- | --- | --- | --- |
| Form γ | Antisolvent | MeOH/EtOAc | 1:10 | 25-30 | Form γ |
| | | MeOH/Acetone | 1:10 | 25-30 | Form γ |
| | | 1,4-Dioxane/IPE | 1:10 | 25-30 | Form γ |
| | | Pyridine/IPE | 1:10 | 25-30 | Form γ |
| | | NMP/IPE | 1:10 | 25-30 | Form γ |
| Form α | Azeotropic Distillation | Toluene/EtOAc | 1:10 | 80-110 | Form γ |
| | | Toluene/ACN | 1:5 | 80-100 | Form γ |
| Amorphous | Azeotropic Distillation | Toluene/ACN | 2:5 | 80-100 | Form γ |

Example 12

Process for the Preparation of Polymorphic Form γ of Perindopril (L)-Arginine 10 g of amorphous Perindopril Arginine salt was exposed to humidity (RH>90%) for 3 hrs. The solid isolated is identified as polymorphic form γ of Perindopril (L)-Arginine.

Example 13

Process for the Preparation of Polymorphic Form γ of Perindopril (L)-Arginine 6 g of amorphous Perindopril Arginine salt was dissolved in toluene (100 ml) and stirred for 10 minutes. The reaction mass was then azeotropically refluxed for 60 minutes. To this solution, acetonitrile (300 ml) was added at reflux temperature and maintained for 60 minutes. The resulting solid was filtered and dried at 50° C. under vacuum. The product obtained was identified as form γ of Perindopril (L)-Arginine.

Example 14

Process for the Preparation of Perindopril Arginine Form α (as Per English Translated Example 1 of WO07099217A1)

1 g of pure Perindopril free acid was dissolved in 4.5 ml of water at 25 to 30° C. To this 0.47 g of (L)-Arginine was added and stirred for 10 min to get clear solution at 25 to 30° C. To this methylcyclohexane (2.5 ml) was added and stirred for 30 minutes at 25 to 30° C. DMSO (13 ml) was added slowly at room temperature. Solid immediately precipitated out, continue stirring for 30 minutes. The solid was filtered and dried at 50 to 55° C. under vacuum for 12 hours.

Example 15

Process for the Preparation of Perindopril Arginine Form α

5 g of Perindopril free acid was dissolved in 25 ml of water at 25 to 30° C. To this (L)-Arginine (2.3 g) was added and stirred for 10 minutes to get clear solution at 25 to 30° C. The reaction mass was cooled to 15 to 20° C. To this cold solution mixture of 12 ml of cyclohexane and 75 ml of dimethylacetamide were added slowly at 15 to 20° C. Solid immediately precipitated out, continue stirring for 1 hour at 15 to 20° C. The solid is filtered and washed with 5 ml of cyclohexane. The wet solid was dried at 50 to 55° C. under vacuum for 12 hours.

The invention claimed is:

1. A process for the preparation of polymorphic form γ of Perindopril (L)-Arginine comprising the steps of:
   a) dissolving Perindopril free acid in water,
   b) adding L-Arginine,
   c) removing the water, and
   d) isolating polymorphic form γ of Perindopril (L)-Arginine.

2. The process according to claim 1, wherein the water is removed by freeze drying or spray drying.

3. A process for the preparation of polymorphic, form γ of Perindopril (L)-Arginine comprising the steps of:
   a) dissolving Perindopril L-Arginine in a solvent,
   b) adding an antisolvent, and
   c) isolating polymorphic form γ of Perindopril (L)-Arginine.

4. The process according to claim 3, wherein the solvent is selected from the group consisting of alcohols, ethers, and polar solvents.

5. The process according to claim 3, wherein the antisolvent is selected from the group consisting of ester solvents, ketone solvents, and ether solvents.

6. A process for the preparation of polymorphic form γ of Perindopril (L)-Arginine comprising the steps of:
   a) suspending Perindopril free acid and L-Arginine in a solvent,
   b) heating the reaction mass to the reflux temperature of the solvent,
   c) adding an anti-solvent, and
   d) isolating polymorphic form γ of Perindopril (L)-Arginine.

7. The process according to claim 6, wherein the solvent for suspension is selected from the group consisting of hydrocarbons, alcohols, and mixtures thereof.

8. The process according to claim 6, wherein the antisolvent is selected from the group consisting of acetonitrile, ethers, and mixtures thereof.

9. The process according to claim 4, wherein the solvent is selected from the group consisting of methanol, 1,4-dioxane, pyridine, and N-methyl pyrrolidone.

10. The process according to claim 5, wherein the antisolvent is selected from the group consisting of ethyl acetate, acetone, and isopropyl ether.

11. The process according to claim 7, wherein the solvent for suspension is selected from the group consisting of toluene, methanol, ethanol, isopropanol, butanol, and mixtures thereof.

12. The process according to claim 8, wherein the antisolvent is selected from the group consisting of acetonitrile, isopropyl ether, diethyl ether, and mixtures thereof.

* * * * *